US011896733B2

(12) United States Patent
Zimnitsky et al.

(10) Patent No.: US 11,896,733 B2
(45) Date of Patent: *Feb. 13, 2024

(54) APPARATUSES, METHODS, AND COMPOSITIONS FOR THE TREATMENT AND PROPHYLAXIS OF CHRONIC WOUNDS

(71) Applicant: KCI Licensing, Inc., San Antonio, TX (US)

(72) Inventors: Dmitry Zimnitsky, Pennington, NJ (US); Jenny Finkbiner, Helotes, TX (US); Blane Sanders, San Antonio, TX (US)

(73) Assignee: 3M Innovative Properties Company, Saint Paul, MN (US)

( * ) Notice: Subject to any disclaimer, the term of this patent is extended or adjusted under 35 U.S.C. 154(b) by 316 days.

This patent is subject to a terminal disclaimer.

(21) Appl. No.: 17/374,662

(22) Filed: Jul. 13, 2021

(65) Prior Publication Data

US 2021/0338885 A1    Nov. 4, 2021

Related U.S. Application Data

(60) Division of application No. 15/982,769, filed on May 17, 2018, now Pat. No. 11,090,409, which is a
(Continued)

(51) Int. Cl.
*A61F 13/00* (2006.01)
*A61M 1/00* (2006.01)
(Continued)

(52) U.S. Cl.
CPC .... *A61L 26/0038* (2013.01); *A61F 13/00068* (2013.01); *A61K 31/085* (2013.01);
(Continued)

(58) Field of Classification Search
CPC .. A61F 2013/00174; A61F 2013/00536; A61F 13/00068; A61F 2013/0091;
(Continued)

(56) References Cited

U.S. PATENT DOCUMENTS 1,355,846 A    10/1920   Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

Alleva R et al: "alpha-Lipoic acid supplementation inhibits oxidative damage, accelerating chronic wound healing in patients undergoing hyperbaric oxygen therapy," Biochemical and Biophysical Research Communications, Academic Press, Inc. Orlando, FL, US, vol. 333, No. 2, Jul. 29, 2005, pp. 404-410, XP027229880, ISSN:0006-291X.
(Continued)

*Primary Examiner* — Adam Marcetich

(57) ABSTRACT

According to an illustrative embodiment a method to promote healing of a wound is provided comprising contacting the wound with a biologically active composition comprising a lipoic acid derivative and gelatin. In another embodiment a wound dressing is provided comprising a scaffold coated with a biologically active composition comprising a lipoic acid derivative. In a further embodiment, a system is provided for treating a tissue site of a patient, the system comprising a reduced-pressure source to supply reduced pressure, a manifold to distribute reduced pressure to a tissue site and a scaffold coated with a biologically active compo-
(Continued)

sition comprising a lipoic acid derivative. Methods for producing such a system and scaffold are also disclosed.

20 Claims, 6 Drawing Sheets

Related U.S. Application Data continuation of application No. 14/135,088, filed on Dec. 19, 2013, now Pat. No. 9,999,702, which is a division of application No. 12/757,562, filed on Apr. 9, 2010, now Pat. No. 8,632,512.

(51) Int. Cl.
*A61L 26/00* (2006.01)
*A61K 31/381* (2006.01)
*A61K 31/085* (2006.01)
*A61K 31/14* (2006.01)
*A61K 31/155* (2006.01)
*A61K 31/785* (2006.01)
*A61K 33/26* (2006.01)

(52) U.S. Cl.
CPC ............ *A61K 31/14* (2013.01); *A61K 31/155* (2013.01); *A61K 31/381* (2013.01); *A61K 31/785* (2013.01); *A61K 33/26* (2013.01); *A61L 26/0066* (2013.01); *A61M 1/915* (2021.05); *A61F 2013/0017* (2013.01); *A61F 2013/00174* (2013.01); *A61L 2300/404* (2013.01); *A61L 2300/414* (2013.01); *A61L 2300/434* (2013.01); *A61M 1/85* (2021.05); *A61M 1/92* (2021.05)

(58) Field of Classification Search
CPC ............ A61F 13/00063; A61F 13/0213; A61F 2013/0054; A61F 13/00; A61F 13/00012; A61F 2013/00931; A61P 17/02; A61P 17/00; A61K 2300/00; A61K 8/0208; A61L 15/44; A61L 15/32; A61L 26/0066; A61L 26/0038; A61L 15/425; A61L 2300/412; A61L 15/325; A61L 2300/254; A61L 2300/404; A61L 2300/45; A61L 2300/608; A61L 24/104; A61L 2400/04
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,035,687 A | 7/1991 | Sandbank |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,591,709 A | 1/1997 | Lindenbaum |
| 5,607,388 A | 3/1997 | Ewall |
| 5,636,643 A | 6/1997 | Argenta et al. |
| 5,645,081 A | 7/1997 | Argenta et al. |
| 5,679,697 A | 10/1997 | Garnett |
| 5,759,570 A | 6/1998 | Arnold |
| 6,071,267 A | 6/2000 | Zamierowski |
| 6,135,116 A | 10/2000 | Vogel et al. |
| 6,166,084 A | 12/2000 | Bloor |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |

(56) References Cited

U.S. PATENT DOCUMENTS

| | | | |
|---|---|---|---|
| 6,803,379 | B2 | 10/2004 | Fernandez-Pol et al. |
| 6,814,079 | B2 | 11/2004 | Heaton et al. |
| 6,814,097 | B2 | 11/2004 | Girouard |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,563,799 | B2 | 10/2013 | Kamakura et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0168400 | A1 | 11/2002 | Jain |
| 2003/0108587 | A1 | 6/2003 | Orgill et al. |
| 2004/0082925 | A1 | 4/2004 | Patel |
| 2004/0138103 | A1 | 7/2004 | Patt |
| 2005/0186260 | A1 | 8/2005 | Narini et al. |
| 2005/0249691 | A1 | 11/2005 | Monks et al. |
| 2005/0281858 | A1 | 12/2005 | Kloke et al. |
| 2006/0034816 | A1 | 2/2006 | Davis et al. |
| 2006/0074108 | A1 | 4/2006 | Gupta |
| 2006/0079852 | A1 | 4/2006 | Bubb et al. |
| 2006/0100586 | A1 | 5/2006 | Karpowicz et al. |
| 2006/0200100 | A1 | 9/2006 | Rosati |
| 2006/0271104 | A1 | 11/2006 | Viola et al. |
| 2007/0055209 | A1 | 3/2007 | Patel et al. |
| 2007/0065473 | A1 | 3/2007 | Miller |
| 2007/0066946 | A1 | 3/2007 | Haggstrom et al. |
| 2007/0071537 | A1 | 3/2007 | Reddy et al. |
| 2007/0073210 | A1 | 3/2007 | Hille et al. |
| 2007/0128296 | A1 | 6/2007 | Hoekstra et al. |
| 2007/0134305 | A1 | 6/2007 | Zilberman |
| 2007/0149487 | A1 | 6/2007 | Pang et al. |
| 2007/0185426 | A1 | 8/2007 | Ambrosio et al. |
| 2007/0185463 | A1 | 8/2007 | Mulligan |
| 2007/0225663 | A1 | 9/2007 | Watt et al. |
| 2007/0237812 | A1 | 10/2007 | Patel et al. |
| 2007/0299410 | A1 | 12/2007 | Eknoian et al. |
| 2008/0038300 | A1* | 2/2008 | Jaspers ............... A61F 13/0223 424/78.17 |
| 2008/0260808 | A1 | 10/2008 | Pinna et al. |
| 2008/0275409 | A1 | 11/2008 | Kane et al. |
| 2009/0005722 | A1* | 1/2009 | Jennings-Spring ........................ A61F 13/00063 604/20 |
| 2009/0035289 | A1 | 2/2009 | Wagner et al. |
| 2009/0157017 | A1 | 6/2009 | Ambrosio |
| 2009/0177133 | A1 | 7/2009 | Kieswetter et al. |
| 2009/0220450 | A1 | 9/2009 | Green et al. |
| 2009/0280162 | A1 | 11/2009 | Wegmann et al. |
| 2010/0015200 | A1 | 1/2010 | McClain et al. |
| 2010/0016767 | A1 | 1/2010 | Jones et al. |
| 2010/0249733 | A9 | 9/2010 | Blott et al. |
| 2010/0255109 | A1 | 10/2010 | Kim et al. |
| 2010/0260823 | A1 | 10/2010 | Alupei et al. |
| 2010/0278784 | A1* | 11/2010 | Pojasek ............... A61K 8/671 424/93.7 |
| 2011/0136669 | A1* | 6/2011 | Liebmann ............... A01N 25/10 424/443 |
| 2011/0213022 | A1 | 9/2011 | Nelson |
| 2011/0263504 | A1* | 10/2011 | Cerami ............... A61P 39/00 435/320.1 |
| 2011/0306755 | A1 | 12/2011 | Bhatia et al. |
| 2012/0220962 | A1 | 8/2012 | Hsu et al. |
| 2012/0245540 | A1 | 9/2012 | Zimnitsky et al. |
| 2013/0129710 | A1 | 5/2013 | Nordhaus et al. |
| 2013/0158515 | A1 | 6/2013 | Austen, Jr. |
| 2013/0184220 | A1* | 7/2013 | Duft ............... C12N 15/1138 514/18.6 |
| 2014/0141050 | A1 | 5/2014 | Ploger et al. |
| 2014/0163491 | A1 | 6/2014 | Schuessler et al. |
| 2014/0199367 | A1 | 7/2014 | Orofino |
| 2015/0080788 | A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 801170 A | 9/1958 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 2005-132725 A | 5/2005 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/10808 A1 | 3/1997 |
| WO | 97/18007 A1 | 5/1997 |
| WO | 99/13793 A1 | 3/1999 |
| WO | 0024378 A1 | 5/2000 |
| WO | 0059424 A1 | 10/2000 |
| WO | 0100157 A1 | 1/2001 |
| WO | 02085386 A2 | 10/2002 |
| WO | 2006034568 A1 | 4/2006 |
| WO | 2006/058318 A2 | 6/2006 |
| WO | 2006/095193 A2 | 9/2006 |
| WO | 2007092405 A2 | 8/2007 |
| WO | 2007/106590 A2 | 9/2007 |
| WO | 2008057600 A2 | 5/2008 |
| WO | 2008091521 A2 | 7/2008 |
| WO | 2008142569 A2 | 11/2008 |
| WO | 2009/088926 A1 | 7/2009 |
| WO | 2009137074 A1 | 11/2009 |
| WO | 2009158500 A2 | 12/2009 |
| WO | 2010017282 A1 | 2/2010 |
| WO | 2012162098 A2 | 11/2012 |

OTHER PUBLICATIONS

International Preliminary Report on Patentability for PCT/US2011/031441 dated Aug. 4, 2015.
International Search Report and Written Opinion for corresponding application PCT/US2014/025000 dated Jul. 1, 2014.
Supplementary European Search Report for corresponding European Application No. EP08869720 dated Nov. 23, 2012.
Alpha Lipoic Acid 200 mg; http://www.seacoast.com/supplement/natural-factors-alpha-lipoic-acid-200-m-60-caps-13; viewed Mar. 30, 2011.
Inoguchi, T, et al., ""Protein Kinase C-Dependent Increase in Reactive Oxygen Species (ROS) Production in Vascular Tissues of

(56) References Cited

OTHER PUBLICATIONS

Diabetes: Role of Vascular NAT(P)H Oxidase"" J Am Nephr 227-232 (2003).
James et al, "Antioxidant Characteristics of Chronic Wound Fluid" Br J Dermatol 145(1): 185-6 (2001).
James et al., "Evidence of Oxidative Stress in Chronic Venous Ulcers" Wound Repair Regen 11(3): 172-6 (2003).
Mendez, et al., "Fibroblasts Cultured from Venous Ulcers Display Cellular Characteristics of Senescence" J Vasc Surg 28(5): 876-83 (1998).
Novo, "Redox Mechanisms in Hepatic Chronic Wound Healing and Fibrogenesis" Fibrosenesis Tissue Repair 1 (1):5 (2008).
Rojas "Patients with Chronic Leg Ulcers Show Diminished Levels of Vitamins A and E, Carotenes and Zinc" Dermatol Surg 25(8):601-4 (1999).
Wlaschek "Oxidative Stress in Chronic Venous Leg Ulcers" Wound Repari Regen 13(5):452-61 (2005).
Eming "Inflammation in Wound Repair: Molecular and Cellular Mechanisms" Journal of Investigative Dermatology (2007).
Yager "Wound Fluids from Human Pressure Ulcers Contain Elevated Matrix Metalloproteinase Levels and Activity Compared to Surgical Wound Fluids" The Society for Investigative Dermatology 2006; 107(15): 744-748.
Sarisoezen "The Effects of Vitamins E and C on Fracture Healing in Rats" The Journal of International Medical Research 2002; 30:309-313.
Gray "Does Vitamin C Supplementation Promote Pressure Ulcer Healing:" J WOCN 2003; 30:245-9.
Jagetia "Ascorbic Acid Increases Healing of Excision Wounds of Mice Whole Body Exposed to Different Doses of G-Radiation" Burns 33 (2007) 484-494.
Lim "Dietary Supplementation of N- acetylcysteine Enhances Early Inflammatory Response During Cutaneous Wound Healing in Protein Malnourished Mice" Journal of Nutritional Biochemistry 17 (2006) 328-336.
Cardoso et al "Influence of Topical Administration of n -3 and n -6 Essential and n -9 Nonessential Fatty Acids on the Healing of Cutaneous Wounds" Wound Repair and Regeneration, 2004; 12-235-243.
Henriksen, Exercise Training and the Antioxidant alpha-lipoic Acid in the Treatment of Insulin Resistance and Type 2 Diabetes Free Radic Biol Med 2006 40(1):3-12.
Ames "Delaying the Mitochondrial Decay of Aging with Acetylcarnitine" Ann NY Acad Sci 2004 1033:108-116.
Holmquist "Lipoic Acid as a Novel Treatment for Alzheimer's Disease and Related Dementias" Pharmacology & Therapeutics 113 1 (2007): 154-164.
Kofuji "Stabilization of a-lipoic Acid by Complex Formation with Chitosan" Food Chemistry 2008; 109:167-171.
Alleva, et al., "a-Lipoic Acid Modulates Extracellular Matrix and Angiogenesis Gene Expression in Non-Healing Wounds Treated with Hyperbaric Oxygen Therapy." Mol Med 14 (3-4), 2008, 175-183.
Frank et al. "Large induction of the chemotactic cytokine RANTES during cutaneous wound repair: a regulatory role for nitric oxide in keratinocyte-derived RANTES expression," Biochem J. (2000) 347, (pp. 265-273) (9 pages).
Witte, et al., "Nitric oxide enhances experimental wound healing in diabetes," British Journal of Surgery 2002, 89 (pp. 1594-1601) (8 pages).
Lee et al, "Impaired wound healing and angiogenesis in eNOS-deficient mice," The American Physiological Society 1999/Am J. Physiol Heart Circ Physiol 277:1600-1608, 1999. (10 pages).
Najjar et al., "Evaluation of Poly-N-Acetyl Glucosamine as a Hemostatic Agent in Patients Undergoing Cardiac Catheterization: A Double-Blind Randomized Study," The Journal of TRAUMA®, Injury, Infection, and Critical Care; Jul. 2004 (Supplement) (4 pages).
Musalmah et al., "Effect of vitamin E on plasma malondialdehyde, antioxidant enzyme levels and the rates of wound closures during wound healing in normal and diabetic rats," Asia Pacific J. Clin Nutr (2002) 11 (Suppl): S448-S451 (4 pages).
Boykin, Jr. et al., "Diabetes-Impaired Wound Healing Predicted By Urinary Nitrate Assay—A Preliminary, Retrospective Study, " available online at URL: http://www.hitechno.com/Final/links/DB.htm>; Wounds 11(3): 62-69, 1999 Health Management Publications, Inc. (8 pages).
International Search Report and Written Opinion date dated Feb. 17, 2009; PCT Application No. PCT/US2008/088636.
Lateef et al., "Pretreatment of diabetic rats with lipoic acid improves healing of subsequently-induced abrasion wounds", Arch Dermatol Res (2005) 297:75-83 DOI 10.1007/s00403 -005-0576 -6. (9 pages).
International Search Report and Written Opinion dated Jun. 9, 2011; International PCT Application No. PCT/US2011/031441.
European Examination Report for related application 11715141.5, dated May 4, 2018.
European Examination Report for related application 14720324.4, dated Sep. 20, 2018.
De Paula et al, "Physical and Chemical Characterization of Poly(hexamethylene biguanide) Hydrochloride," 2011, 928-941.
Office Action for related U.S. Appl. No. 14/883,483, dated Aug. 20, 2019.
Advisory Action for related U.S. Appl. No. 14/206,914, dated Sep. 18, 2019.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983, dated Nov. 23, 1995.
PCT International Search Report for PCT International Application PCT/GB98/02713, dated Jan. 8, 1999.
PCT Written Opinion; PCT International Application PCT/GB98/02713, dated Jun. 8, 1999.
PCT International Examination and Search Report, PCT International Application PCT/GB96/02802, dated Jan. 15, 1998 & dated Apr. 29, 1997.
PCT Written Opinion, PCT International Application PCT/GB96/02802, dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.

(56) References Cited

OTHER PUBLICATIONS

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

APPARATUSES, METHODS, AND COMPOSITIONS FOR THE TREATMENT AND PROPHYLAXIS OF CHRONIC WOUNDS

RELATED APPLICATIONS

This application is a divisional of U.S. patent application Ser. No. 15/982,769, filed May 17, 2018, which is a continuation of U.S. patent application Ser. No. 14/135,088, filed Dec. 19, 2013, now U.S. Pat. No. 9,999,702, which is a divisional of U.S. patent application Ser. No. 12/757,562, filed Apr. 9, 2010, now U.S. Pat. No. 8,632,512, all of which are hereby incorporated herein by reference in their entirety.

BACKGROUND

The present invention relates generally to medical treatment systems, and more particularly, medical dressings, systems, and methods employing alpha-lipoic acid and its pharmaceutically acceptable salts and derivatives, for the preparation and composition applied to a substrate for treatment or prophylaxis of chronic wounds.

Typical procedures for treating chronic wounds such as, for example, venous ulcers, diabetic ulcers and pressure sores, include the use of absorbent dressings or hydrocolloid gels. Additionally, since most chronic wounds are infected, many wound dressings contain antimicrobial agents, such as silver or iodine, to either create a barrier to microorganisms or reduce microbial load. These treatments are used more for managing the wound environment and moisture balance than actively promoting wound healing.

Inflammation and the timely release of reactive oxygen species (ROS) are critical for normal wound repair and, together with proteolytic and other cytotoxic enzymes, serve to kill ingested bacteria and prevent wound infection. However, due to other circumstances such as patient nutrition, co-morbidities (smoking, diabetes), or poor blood circulation due to patient positioning, the inflammatory phase may last too long resulting in the creation of excess ROS that actually damage surrounding tissue including healthy tissue forming within the wound. Excess ROS, also known as "free radicals," can be detrimental to tissue because they also damage cells and extracellular matrix components such as collagen. Additionally, ROS can act as signaling molecules to recruit matrix metallo proteases (MMPs) and other proteases to the wound site. Normal endogenous levels of MMPs are essential for tissue remodeling during the wound healing process. However, in excess, they continually break down the new tissue that is formed. This leads to a wound that either does not heal quickly or becomes "stalled." Excess levels of ROS and MMPs create a sustained state of inflammation thereby preventing the progression of normal wound healing.

Elevated levels of MMPs have been remedied by preventing activation of MMPs or by use of MMP inhibitors. Some wound dressings on the market use various forms of natural collagen as a sacrificial substrate for MMPs because the collagen also provides the mechanical properties (integrity) necessary to form the dressing. Topical application of antioxidants to a wound may reduce ROS levels, subsequently helping a chronic wound to re-enter a normal healing state.

SUMMARY

According to an illustrative embodiment, a method for promoting healing of a wound is provided comprising contacting a wound site with a biologically active composition comprising a lipoic acid derivative and, optionally, gelatin. Biologically active compositions, such as those provided, may be formulated for example as a solution, a cream or a gel. In certain aspects, a biologically active composition is coated on the surface of a wound dressing (e.g., a porous scaffold), which can be positioned at a wound site. Methods for producing a scaffold coated with a biologically active composition are also provided.

According to another illustrative embodiment, a system is provided for treating a wound at a tissue site of a patient that includes a reduced-pressure source to supply reduced pressure, a distribution manifold, and a scaffold adapted for placement adjacent the wound. The system also includes a drape to cover the sealant and further form the substantially sealed space. The scaffold is coated with a biologically active composition including a lipoic acid derivative or any of its pharmaceutically acceptable salts and derivatives for treatment or prophylaxis of chronic wounds. The scaffold may also comprise a collagen coating such a coating comprising gelatin.

According to another illustrative embodiment, an apparatus includes a distribution manifold and a scaffold adapted for placement adjacent the wound. The scaffold is coated with a biologically active composition including a lipoic acid derivative or any of its pharmaceutically acceptable salts and derivatives.

According to another illustrative embodiment, a method for treating a tissue site of a patient includes applying a dressing to the wound. A dressing may include a composition comprising a lipoic acid derivative and, optionally, gelatin. The dressing includes, in some aspects, a distribution manifold and a scaffold adapted for placement adjacent the wound. In certain embodiments, the dressing also includes a drape for covering the dressing and further forming the substantially sealed space.

The present invention provides the use of alpha-lipoic acid and its pharmaceutically acceptable salts and derivatives, for the preparation of a composition for treatment or prophylaxis of chronic wounds. In certain aspects, a lipoic acid derivative is formulated with gelatin in a composition for treating a wound.

In a further embodiment, the invention provides a kit or pouch comprising wound dressing components. Such a kit can, for example, comprise one or more of a wound dressing comprising a biologically active composition including alpha-lipoic acid and, optionally, gelatin, a drape, a reduced pressure manifold, one or more fluid conduits (e.g., tubes) and instructions for use of the kit components. In certain aspects, the components of the kit or pouch are sterilized, for example by gamma irradiation.

DETAILED DESCRIPTION

Figure 1:
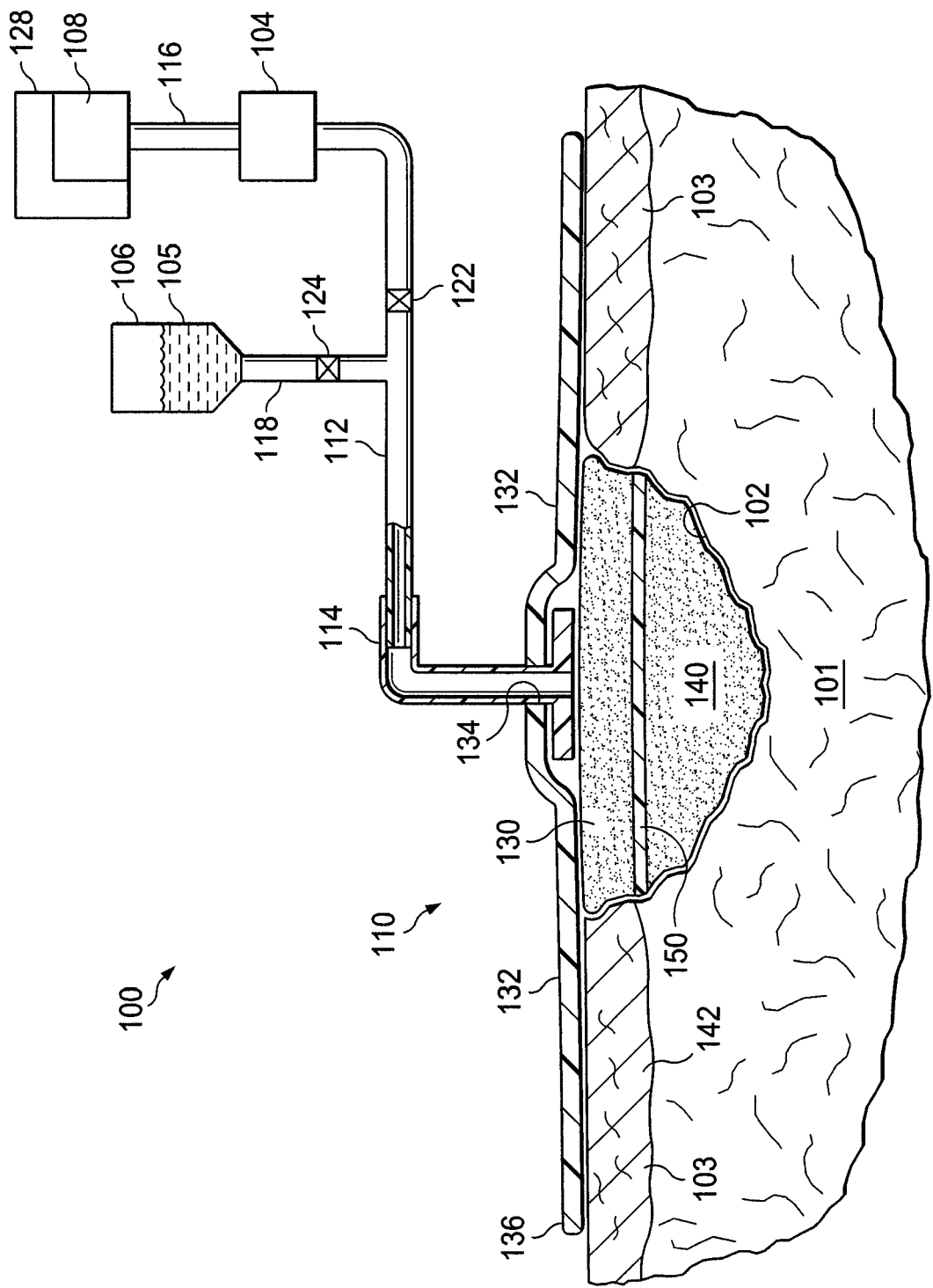
FIG. 1 is a schematic, cross-sectional view of a reduced-pressure treatment system including wound dressing that utilizes a first distribution manifold according to one illustrative embodiment.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein includes, without limitation, a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location. The tissue may be that of any mammal, such as a mouse, rat, rabbit, cat, dog, pig, or primate, including humans, that are being treated as patients. Also, the wound at the tissue site may be due to a variety of causes, including trauma, surgery, degeneration, and other causes.

The term "biologically active composition" as used herein refers to a composition formulated with a lipoic acid derivative and, optionally, a gelatin. Such compositions may be formulated in any pharmaceutically acceptable carrier and will typically comprise an amount of lipoic acid derivative effective to reduce reactive oxygen species and inflammation at a tissue site. Gelatin for use according to the invention may be from any tissue source, such as from bovine, equine, or porcine tissues. Formulations and components for biologically active compositions are further detailed below.

Figure 2:
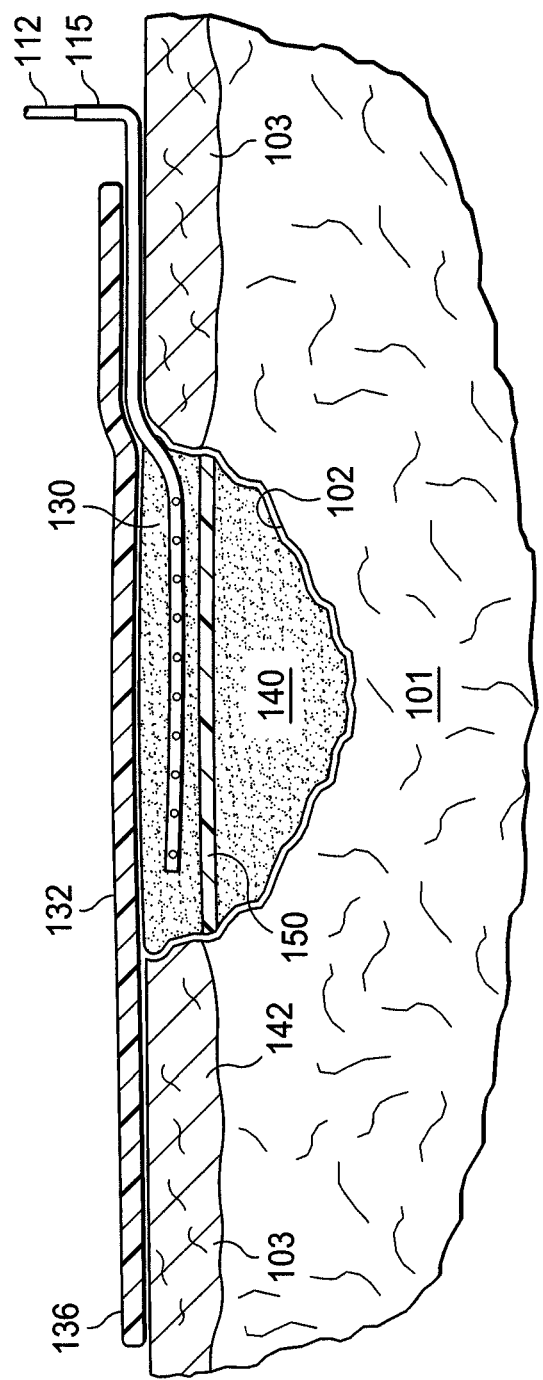
FIG. 2 is a schematic, cross-sectional view of the reduced-pressure treatment system of FIG. 1 including wound dressing that utilizes a second distribution manifold according to another illustrative embodiment.

Referring to FIGS. 1 and 2, a reduced pressure treatment system 100 for applying a reduced pressure to a tissue site 101 of a patient according to an illustrative embodiment where the tissue site includes wound 102 surrounded by healthy tissue including, without limitation, the epidermis 103 of such tissue. The system 100 comprises a canister 104 having a filter (not shown) contained within the canister 104 and a fluid supply 106 for delivering fluid 105 to the tissue site 101. The canister 104 is positioned in fluid communication with a reduced pressure source 108 and a reduced pressure dressing 110 that is positioned at the tissue site 101. The reduced pressure dressing 110 is fluidly connected to the canister 104 by a first conduit 112. The first conduit 112 may fluidly communicate with the reduced pressure dressing 110 through a tubing adapter 114. A second conduit 116 fluidly connects the canister 104 with the reduced pressure source 108.

The canister 104 may be a fluid reservoir, or collection member, to filter or hold exudates and other fluids removed from the tissue site 101. In one embodiment, the canister 104 and the reduced-pressure source 108 are integrated into a single housing structure. The fluid supply 106 is fluidly connected to the reduced pressure dressing 110 by a third conduit 118 that may be connected directly to the reduced pressure dressing 110 (not shown) or indirectly via the first conduit 112 which requires valves 122 and 124 for controlling the delivery of reduced pressure from the reduced pressure source 108 and/or fluid 105 from the fluid supply 106, respectively. The fluid 105 may be any gas or liquid, and may contain growth factors, healing factors, or other substances to treat the wound 102 at the tissue site 101. For example, the fluid 105 may be water, saline, or dye saline.

In the embodiment illustrated in FIG. 1, the reduced pressure source 108 is an electrically-driven vacuum pump. In another implementation, the reduced pressure source 108 may instead be a manually-actuated or manually-charged pump that does not require electrical power. The reduced pressure source 108 instead may be any other type of reduced pressure pump, or alternatively a wall suction port such as those available in hospitals and other medical facilities. The reduced pressure source 108 may be housed within or used in conjunction with a reduced pressure treatment unit 128, which may also contain sensors, processing units, alarm indicators, memory, databases, software, display unites, and user interfaces that further facilitate the application of reduced pressure treatment to the tissue site 101. In one example, a sensor or switch (not shown) may be disposed at or near the reduced pressure source 108 to determine a source pressure generated by the reduced pressure source 108. The sensor may communicate with a processing unit that monitors and controls the reduced pressure that is delivered by the reduced pressure source 108.

The reduced pressure dressing 110 includes a distribution manifold 130 adapted to be positioned at the tissue site 101, and a drape 132 that covers the distribution manifold 130 to maintain reduced pressure beneath the drape 132 at the tissue site 101. The reduced pressure dressing 110 may also include a separate scaffold 140, wherein the scaffold is coated with a biologically active composition comprising a lipoic acid derivative, and is positioned within the wound 102 in fluid communication with the distribution manifold 130. The system may further include a release layer 150 positioned in fluid communication between the distribution manifold 130 and the scaffold 140. The release layer 150 may include a release material such as a hydro-gel foaming material or water-soluble polymer. The drape 132 includes an aperture 134 through which the tubing adapter 114 extends to provide fluid communication between the conduit 112 and the distribution manifold 130. The drape 132 further includes a periphery portion 136 that may extend beyond a perimeter of the tissue site 101 and may include an adhesive or bonding agent (not shown) to secure the drape 132 to tissue adjacent the tissue site 101. In one embodiment, the adhesive disposed on the drape 132 may be used to provide a seal between the epidermis 103 and the drape 132 to prevent leakage of reduced pressure from the tissue site 101. In another embodiment, a seal layer (not shown) such as, for example, a hydrogel or other material may be disposed between the drape 132 and the epidermis 103 to augment or substitute for the sealing properties of the adhesive.

The drape 132 may be any material that provides a pneumatic or fluid seal. The drape 132 may, for example, be an impermeable or semi-permeable, elastomeric material. "Elastomeric" means having the properties of an elastomer, and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of drape materials include a silicone drape, 3M Tegaderm® drape, acrylic drape such as one available from Avery Dennison, or an incise drape.

Referring to FIG. 2, another embodiment of the reduced pressure dressing 110 is shown wherein the conduit connector 114 that penetrates the drape 132 is replaced by a perforated tube 113 having a plurality of apertures 115 in one end that are in fluid communication with the distribution manifold 130. The first conduit 112 is fluidly coupled to the other end of the perforated tube 113 for delivering reduced pressure or other fluids to the wound 102 as described above via the distribution manifold 130 and the scaffold 150. The distribution manifold 130 of the reduced pressure dressing 110 may be adapted to fully contact (not shown) or partially contact the wound 102 of the tissue site 101 being treated by the reduced pressure dressing 110, in which case the scaffold 140 covers the remaining portion of the wound 102.

Figure 3:
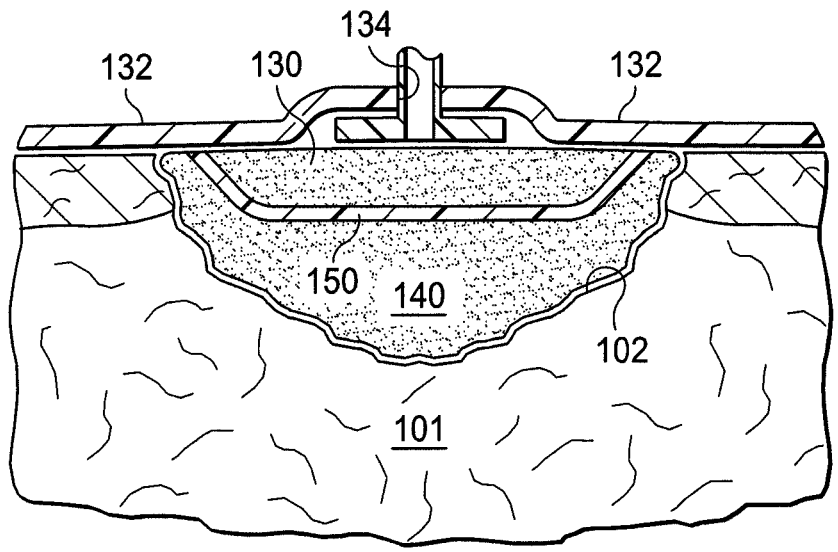
FIG. 3 is a schematic, cross-sectional view of the reduced-pressure treatment system of FIG. 1 including wound dressing that utilizes a third distribution manifold according to another illustrative embodiment.

In another embodiment shown in FIG. 3, the distribution manifold 130 of the reduced pressure dressing 110 contacts only the scaffold 140 but not any portion of the wound 102. In this embodiment, the first conduit 112 delivers reduced pressure or other fluids via the distribution manifold 130 to the scaffold 140 and ultimately the wound 102. In either embodiment, the distribution manifold 130 and the scaffold 140 may be any size, shape, or thickness depending on a variety of factors, such as the type of treatment being implemented or the nature and size of the tissue site 101 or the wound 102. For example, the size and shape of the scaffold 140 may be customized by a user to fill or partially fill the tissue site 101 or the wound 102. The distribution manifold 130 may have, for example, a square shape, or may be shaped as a circle, oval, polygon, an irregular shape, or any other shape.

The distribution manifold 130, scaffold 140, and the release layer 150 (collectively referred to as the "layers") all include a plurality of flow channels of sufficient size to allow distribution of reduced pressure within the reduced pressure dressing 110 and to the wound 102. The flow channels provided in each of the layers may be an inherent characteristic of the material provided in that layer (e.g., a naturally porous material), or the flow channels may be chemically, mechanically, or otherwise formed in the material prior to or after assembly of the three layers. The placement of the layers adjacent one another allows the flow channels in one layer to fluidly communicate with the flow channels in the adjacent layer. For example, the relative positioning or connection of the layers as described above allow the plurality of flow channels of the scaffold 140 to fluidly communicate with the plurality of flow channels of the release layer 150, which are capable of fluidly communicating with the plurality of flow channels of the distribution manifold 130.

The term "manifold" as used herein generally refers to a substance or structure that is provided to assist in applying reduced pressure to, delivering fluids to, or removing fluids from a tissue site. A manifold typically includes a plurality of flow channels or pathways that are interconnected to improve distribution of fluids provided to and removed from the area of tissue around the manifold. Examples of manifolds may include without limitation devices that have structural elements arranged to form flow channels, cellular foam such as open-cell foam, porous tissue collections, and liquids, gels and foams that include or cure to include flow channels. In one illustrative embodiment, the distribution manifold 130 is a foam material that distributes reduced pressure to the tissue site 101 when the distribution manifold 130 is in contact with or near the tissue site 101. The foam material may be either hydrophobic or hydrophilic.

In one non-limiting example, the distribution manifold 130 is an open-cell, reticulated polyurethane foam such as GranuFoam® dressing available from Kinetic Concepts, Inc. of San Antonio, Texas. In the example in which the distribution manifold 130 is made from a hydrophilic material, the distribution manifold 130 also functions to wick fluid away from the tissue site 101, while continuing to provide reduced pressure to the tissue site 101 as a manifold. The wicking properties of the distribution manifold 130 draw fluid away from the tissue site 101 by capillary flow or other wicking mechanisms. To adequately distribute the reduced pressure and wick fluid away from the tissue site 101, the GranuFoam® dressing in one embodiment has a porosity with pore sizes ranging from about 400-600 microns. An example of a hydrophilic foam is a polyvinyl alcohol, open-cell foam such as V.A.C. WhiteFoam® dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity. In one embodiment, the distribution manifold 130 may be constructed from bioresorbable materials that do not have to be removed from a patient's body following use of the reduced pressure dressing 110. Suitable bioresorbable materials may include, without limitation, collagen or a polymeric blend of polylactic acid (PLA) and polyglycolic acid (PGA). The polymeric blend may also include, without limitation, polycarbonates, polyfumarates, and capralactones.

Scaffolds, such as scaffold 140 of FIGS. 1-3, may be formed from biologic or synthetic scaffold materials. Scaffolds are used in the field of tissue engineering to support protein adhesion and cellular ingrowth for tissue repair and regeneration. In certain aspects, a scaffold may further comprise a biologically active composition, such as those detailed herein (e.g., a composition comprising a lipoic acid derivation and gelatin). The current state of the art in scaffold technology relies upon the inherent characteristics of the surrounding tissue space for the adsorption of proteins and migration of cells. The scaffold 140 provides physical guidance to direct the pathway of fluid flow within the wound 102 at the tissue site 101 creating avenues for the movement and migration of adhesive proteins and cells, respectively, which are integral to the establishment of a provisional matrix in predetermined patterns of organization within the tissue space. Within this context, scaffolds serve to refine the pathways of fluid flow within the tissue space to cellular level patterns from the fluid source to the point(s) of flow initiation within the distribution manifold 130. Thus, the scaffold 140 embodies characteristics of a manifold for refinement of the flow pathways within the wound 102 at the tissue site 101. In certain aspects, a scaffold is a reticulated structure comprising high void fraction for improved bioabsorption properties. Such high void fraction scaffold may also facilitate effective coating with biologically active compositions as detailed herein.

The distribution manifold 130 or portion thereof may further serve as a scaffold for new cell-growth, or a separate scaffold may be used in conjunction with the distribution manifold 130 to promote cell-growth as described above. Thus, a scaffold may also function as a manifold in accordance with the embodiments described herein to administer reduced pressure tissue treatment to a tissue site. Although one skilled in the art recognizes that the distribution manifold 130 may also function as a scaffold, the illustrative embodiments herein describe the use of a separate scaffold structure, the scaffold 140, in conjunction with the distribution manifold 130, wherein the scaffold also functions as a manifold. In such embodiments, the separate manifold may also be coated with a biologically active composition comprising a lipoic acid derivative. The scaffold and/or manifold may be also be infused with, coated with, or comprised of cells, growth factors, extracellular matrix components, nutrients, integrins, or other substances to promote cell growth.

In general a scaffold may be composed of any of the materials used to form a manifold. Nonlimiting examples of suitable scaffold materials include extracellular matrix proteins such as fibrin, collagen or fibronectin, and synthetic or naturally occurring polymers, including bioabsorbable or non-absorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyorthoesthers, polyethylene glycols, poloxamers, polyphosphazenes, polyanhydrides, polyamino acids, polyacetals, polycyanoacrylates, polyurethanes (e.g., GranuFoam®), polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon. The scaffold can also comprise ceramics such as hydroxyapatite, coralline apatite, calcium phosphate, calcium sulfate, calcium carbonate or other carbonates, bioglass, allografts, autografts, xenografts, decellularized tissues, or composites of any of the above. In particular embodiments, the scaffold comprises collagen (e.g., Biostep™ or Pomogran™ scaffolds), polylactic acid (PLA), polyglycolic acid (PGA), polylactide-co-glycolide (PLGA), a polyurethane, a polysaccharide, an hydroxyapatite, or a polytherylene glycol. Additionally, the scaffold can comprise combinations of any two, three or more materials, either in separate or multiple areas of the scaffold, combined noncovalently or covalently (e.g., copolymers such as a polyethylene oxide-polypropylene glycol block copolymers, or terpolymers), or combinations thereof. Suitable matrix materials are discussed in, for example, Ma and Elisseeff, 2005, and Saltzman, 2004. The scaffold 140 may be manufactured by any of the following processes: salt leaching, freeze-drying, phase-separation, weaving fibers, bonding non-woven fibers, foaming, or any other suitable manufacturing method for the selected material.

The scaffold 140 may be any porous, bioresorbable material that is capable of accepting and/or integrating new tissue growth into the scaffold 140 as described above. The pores of the scaffold 140 are preferably interconnected to define the plurality of flow channels within the scaffold 140, but additional flow channels may be provided by mechanically, chemically, or otherwise forming the flow channels within the scaffold 140. As further detailed below, the exterior and interior surfaces (e.g., flow channels) of the scaffold may be coated with a biologically active composition comprising a lipoic acid derivative, and options gelatin. The pore sizes associated with the scaffold 140 are typically between about 50 and 500 microns, and more preferably between about 100 and 400 microns. Pore sizes below 50 microns tend to inhibit or prevent tissue growth. According, scaffolds for use according to the invention, comprise a pore size large enough such that pores remain larger than about 50 microns after the scaffold is coated with a biologically active composition. In one embodiment, the preferred average pore size of pores within the scaffold after coating is about 100 microns.

The release layer 150 minimizes points of contact between the distribution manifold 130 and the scaffold 140. In one embodiment, the release material 150 will prevent any contact between the distribution manifold 130 and the scaffold 140. By minimizing contact between the distribution manifold 130 and the scaffold 140, the release material 150 serves as a barrier to tissue in-growth from the scaffold 140 into the distribution manifold 130. The release layer 150 may also serve as a binder and a release agent for the distribution manifold 130 and the scaffold 140. The release layer 150 is preferably either a hydrogel-forming material or a water-soluble polymer. The hydrogel-forming material may be any suitable material that is capable of accepting and/or forming a liquid or gel-like substance after exposure to water or other fluids for a specified period of time.

The plurality flow channels of the release layer 150 allows the distribution of reduced pressure from the distribution manifold 130 to the scaffold 140, and further allows passage of any fluids being provided to or being removed from the wound 102. The plurality of flow channels may be an inherent characteristic of the release layer 150 (i.e. interconnected pores or other flow channels within the material itself), or mechanically, chemically, or otherwise formed in the release layer 150. Regardless of whether pores, voids, apertures, or some combination thereof are used to define the plurality of flow channels in the release layer 150, the porosity of the release layer 150 may be less than the porosity of the scaffold 140 to minimize in-growth of tissue into the release layer 150. The porosity of the release layer 150 may be controlled by limiting the size of the pores, voids, or apertures, or by controlling the number (i.e. density) of pores, voids, or apertures disposed in the release layer 150. The porosity of the release layer 150, however, must remain high enough to allow distribution of reduced pressure and the flow of fluids through the release layer 150.

In operation, the three layers of the reduced pressure dressing 110 are trimmed if necessary to match the shape and size of the wound 102. In many cases, the wound 102 may be an open wound, burn, or other-damaged tissue, but the tissue site 101 may similarly be a site that contains healthy tissue upon which it is desired to grow additional tissue. The reduced pressure dressing 110 is placed adjacent the wound 102 such that the scaffold 140 is in contact with the wound 102. The multiple layers of the reduced pressure dressing 110 may be laminated, bonded, or otherwise connected, but the layers may also be separate from one another. If certain of the layers are not connected to one another, the various layers may be placed individually such that the scaffold 140 is in contact with the tissue site, the release layer 150 is in contact with the scaffold 140, and the distribution manifold 130 is in contact with the release layer 150.

After positioning the reduced pressure dressing 110, a reduced pressure is delivered from the reduced pressure source 108 to the manifold 130. The reduced pressure is distributed through the plurality of flow channels associated with the manifold 130 to the plurality of flow channels associated with the release layer 150. The reduced pressure is then distributed to the plurality of flow channels associated with the scaffold 140. As reduced pressure reaches the wound 102, fluids at the wound 102 such as wound exudate may be drawn through the plurality of flow channels in all the layers and removed from the reduced pressure dressing 110. The canister 104 collects exudate and protect the reduced pressure source 108. In addition to allowing distribution of reduced pressure and the withdrawal of fluids from the wound 102, the plurality of flow channels of the three layers may be used to distribute fluids such as irrigation fluids, medication, antimicrobials, antibacterials, antivirals, and growth factors to the wound 102.

The application of reduced pressure to the wound 102 induces new tissue growth. Some of the mechanisms by which new tissue growth is promoted include micro-deformation of the tissue, epithelial migration, and improved blood flow. These factors contribute to increasing the development of granulation tissue at the tissue site, which results in new tissue growth. While the discussion of providing reduced pressure tissue treatment often refers to "delivering" reduced pressure to the tissue site, it should be apparent to a person of ordinary skill in the art that delivery of reduced pressure typically involves creating a pressure differential between the reduced pressure source 108 and the wound 102. The pressure differential (with a lower pressure at the reduced pressure source 108 than at the wound 102) creates an initial fluid flow from the wound 102 toward the reduced pressure source 108. Once the pressure at the wound 102 nears or equals that of the pressure at the reduced pressure source 108, the reduced pressure may be maintained at the tissue site due to the fluid connection with the reduced pressure source 108 and the sealing function of the drape 132.

As new tissue forms under the influence of reduced pressure, the new tissue is permitted to grow into the scaffold 140. The material chosen for the scaffold 140 preferably supports and encourages new tissue growth. Since the scaffold 140 will remain at the tissue site following the administration of reduced pressure tissue treatment, it is preferred that new tissue penetrates the scaffold as much as possible. It has been observed that under the influence of reduced pressure, new tissue may penetrate up to 1 mm (thickness) of the scaffold 140 in a period of two days. Since the thickness of the scaffold 140 in some embodiments may only be about 1 to 4 mm, it may be desired to remove the distribution manifold 130 and the release layer 150 of the reduced pressure dressing 110 and replace the layers with a new dressing containing a new distribution manifold 130, a new release layer 150, and additional scaffold material. In other words, a new scaffold 140 may be placed on top of the old scaffold 140 following removal of the distribution manifold 130 and the release layer 150. By removing only a portion of the reduced pressure dressing 110 and leaving the scaffold 140, it is possible to incrementally add new tissue growth to the wound 102 as new scaffolds 140 are stacked upon previously inserted scaffolds 140 that are already permeated with new tissue growth.

During the application of reduced pressure, the release material 150 preferably minimizes or prevents contact between the distribution manifold 130 and the scaffold 140 to hinder the growth of new tissue from the scaffold 140 through the release layer 150 and into the distribution manifold 130. New tissue growth into the scaffold 140 is hindered from further growth into the distribution manifold 130 by this separation and by the inherent properties of the release layer 150 as described above. While tissue growth into the distribution manifold 130 may still occur, the growth is minimized, which lessens pain to the patient upon removal of the distribution manifold 130.

Following application of reduced pressure for a selected period of time, the release material 150 may be hydrated by soaking the reduced pressure dressing 110 with water, saline solution, or other fluids. Alternatively, the reduced pressure dressing 110 may be allowed to sit until bodily fluids from the tissue site hydrate the release layer 150. If the release layer 150 is a hydrogel-forming material, the release layer 150 transforms into a gel-like state and typically expands as it hydrates. This allows for easier removal of the distribution manifold 130 from the scaffold 140. Any hydrogel-forming material (or hydrogel) that remains following removal of the manifold 130 may be manually removed or dissolved by the introduction of additional fluids. Alternatively, if the release layer 150 is a water-soluble polymer, it will be dissolved as it absorbs water or other fluids, thus releasing the distribution manifold 130 from the scaffold 140.

Figure 4A:
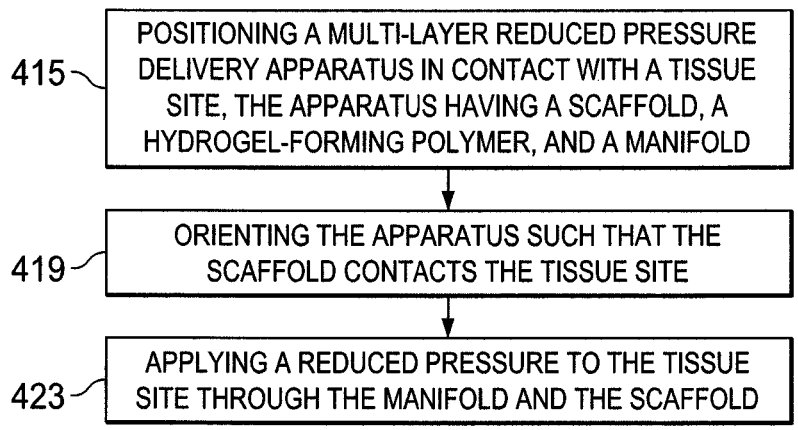
FIG. 4A illustrates a method of promoting new tissue growth at a tissue site according to one embodiment.

Referring to FIG. 4A, a method 411 of promoting tissue growth at a tissue site according to an embodiment of the present invention is illustrated. The method 411 includes positioning a multi-layer reduced pressure delivery apparatus in contact with the tissue site at 415. The reduced pressure delivery apparatus includes a scaffold, a release material, and a manifold. At 419, the apparatus is oriented such that the scaffold contacts the tissue site. A reduced pressure is applied to the tissue site through the manifold and the scaffold at 423.

Figure 4B:
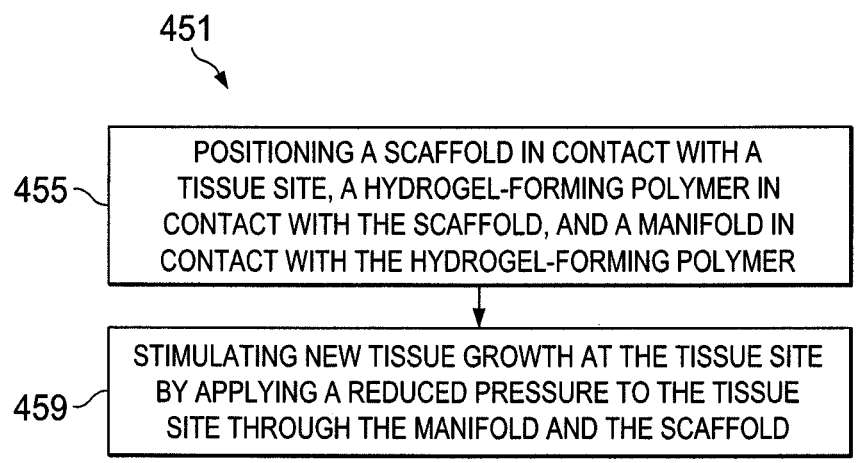
FIG. 4B depicts a method of promoting new tissue growth at a tissue site according to another embodiment.

Referring to FIG. 4B, a method 451 of promoting new tissue growth at a tissue site according to an embodiment of the present invention is illustrated. The method 451 includes at 455 positioning a scaffold in contact with the tissue site, a release material in contact with the scaffold, and a manifold in contact with the release material. At 459, new tissue growth is stimulated at the tissue site by applying a reduced pressure to the tissue site through the manifold and the scaffold.

Figure 5:
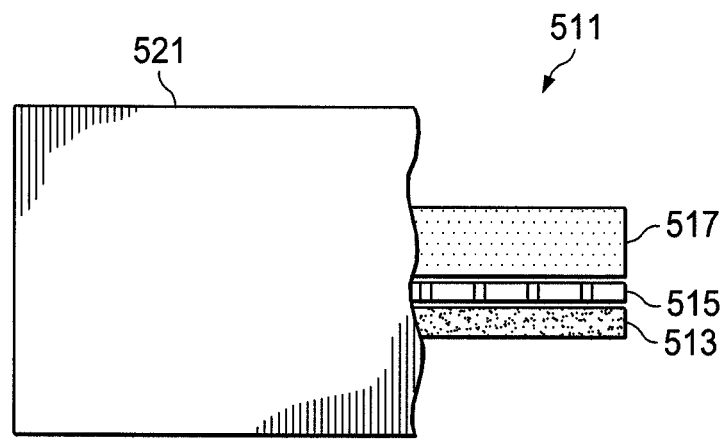
FIG. 5 illustrates a front view of a tissue growth kit according to an embodiment of the present invention.

Referring to FIG. 5, a tissue growth kit 511 for promoting new tissue growth at a tissue site according to an embodiment of the present invention includes a scaffold 513, a release material 515, and a distribution manifold 517. The scaffold 513 includes a first and second side, the first side of the scaffold 513 being adapted to contact the tissue site. The scaffold 513 is similar to the scaffold 140 described previously with reference to FIGS. 1-3. The release material 515 is adapted to contact the second side of the scaffold 513 and is similar to the release layer 150 described previously with reference to FIGS. 1-3. The distribution manifold 517 is adapted to contact the release material 515 to distribute a reduced pressure to the tissue site through the scaffold 513. The distribution manifold 517 is similar to the manifold 130 described previously with reference to FIGS. 1-3. The tissue growth kit 511 may further include a container 521 for housing the scaffold 513, release material 515, and distribution manifold 517 prior to use of the components. The container 521 may be a flexible bag, a box, or any other container suitable for storing the scaffold 513, release material 515, and distribution manifold 517.

While the multi-layer reduced pressure delivery apparatus disclosed herein is used in conjunction with a reduced pressure delivery source to provide reduced pressure tissue treatment to a tissue site, the reduced pressure dressing could also serve as an advanced tissue dressing alone in the absence of reduced pressure application. The same materials, relative positioning, and connectivity between layers may be used in the advanced tissue dressing. Similar to the reduced pressure dressing described herein, the advanced tissue dressing may include a first layer to promote and accept growth of new tissue, a third layer to assist in directing fluids away from the tissue site, and a second layer to facilitate removal of the third layer from the first layer at a selected time. The third layer of the advanced tissue dressing, instead of having a "manifold", may be considered to include a fluid reservoir for collecting and holding fluids exuded by the wound. The materials described herein as being suitable distribution manifold materials are similarly suitable materials for the reservoir of the third layer. The only requirement of the reservoir is that the reservoir should be made from a material that is capable of storing fluids produced by or present at the tissue site.

As discussed above, normal endogenous levels of MMPs are essential for tissue remodeling during the wound healing process. However, in excess, they continually break down the new tissue that is formed. This leads to a wound that either does not heal quickly or becomes "stalled." Excess levels of ROS and MMPs create a sustained state of inflammation thereby preventing the progression of normal wound healing. Accordingly, in certain aspects, the invention provides methods for promoting wound healing by providing a biologically active composition comprising a lipoic acid derivative in an amount effective to reduce the level of ROS and/or reduce inflammation at the wound site and in surrounding tissue.

Figure 6A:
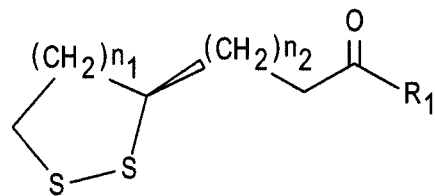
FIG. 6A is a chemical formula of certain derivatives of alpha-lipoic acid or pharmaceutically acceptable salts or derivatives thereof.
Figure 6B:
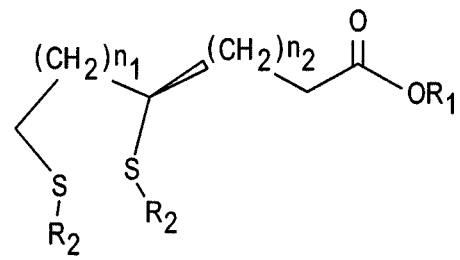
FIG. 6B is a chemical formula of other derivatives of alpha-lipoic acid or pharmaceutically acceptable salts or derivatives thereof.

The term "lipoic acid derivative" refers to molecules structurally related to alpha-lipoic acid, or a salt thereof such as sodium lipoate, that function as an antioxidant in vivo. A wide array of lipoic acid derivatives are known in the art and may be used according to the invention. For example, U.S. Pat. No. 6,887,891 (incorporated herein by reference in its entirety) details a number of lipoic acid derivatives any of which may be used in accordance with the invention. Certain generalized structures for lipoic acid derivative molecules are depicted in FIG. 6A-B. For example, a lipoic acid derivative may have a structure according to FIG. 6A wherein $n_1$ and $n_2$ are, independently, $C_1$-$C_{10}$ alkyl; and $R_1$ is H, $C_1$-$C_{10}$ alkyl, $C_6$-$C_{14}$ aryl, an alkyl ammonium or a protonated amino acid. Likewise, a lipoic acid derivative may have a structure according to FIG. 6B wherein $n_1$ and $n_2$ are, independently, $C_1$-$C_{10}$ alkyl; $R_1$ is H, $C_1$-$C_{10}$ alkyl, $C_6$-$C_{14}$ aryl, an alkyl ammonium or a protonated amino acid; and each of the $R_2$ positions are, independently, H, $C_1$-$C_{10}$ alkyl or $C_6$-$C_{14}$ aryl. Salts of alpha-lipoic acid with inorganic cations such as sodium, alkyl ammonium cations, and other pharmaceutically acceptable cations may be used according to the invention. Additionally, a number of esters and thioesters of alpha-lipoic acid can function as pro-drugs, undergoing hydrolysis to alpha-lipoic acid and dihydrolipoic acid in vivo.

Compositions containing alpha-lipoic acid or the pharmaceutically acceptable salt or derivative thereof may be suitable for local or systemic, oral or parenteral administration. The examples of the administration of alpha-lipoic acid include a formulation comprising of 0.001% to 10% w/v, 0.1% to 10%, or 1% to 5% w/v lipoic acid derivative or salt thereof, in an acceptable carrier. Suitable carriers include, but are not limited to: hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols) as well as gelatin. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA. Biologically active compositions may, in some embodiments, one or more additional active agents.

In certain aspects, topical application of antioxidants (e.g., a lipoic acid derivative) to the wound 102 is used to reduce ROS levels and to facilitate the normal healing process of a chronic wound. Other antioxidants for application in wound healing include ascorbic acid, fatty (linolenic, linoleic, and oleic) acids, and N-acetyl cysteine and such antioxidants may additionally be used in compositions disclosed herein. As demonstrated herein, alpha-lipoic acid and its derivatives are potent antioxidants. Major biological effects of alpha-lipoic acid, for example, include normalizing blood sugar levels, improving nerve blood flow, reducing oxidative stress, alleviating diabetic neuropathy, and protecting membranes. Other advantages of lipoic acid molecules over other antioxidants include high antioxidant activity, the ability to scavenge free radicals in both water and fatty tissues, stability to gamma sterilization, and prolonged shelf-life, which is particularly important for medical device applications. Limited solubility in water and moderate hydrophobicity of alpha-lipoic acid are preferable for formulations that require graduate sustained release of antioxidants. These properties combined with low cost of derivatives such as alpha-lipoic acid make it a preferable solution for treatment of chronic wounds in general, and for incorporation into wound dressing such as the scaffold 140 of the wound dressing 110 described above.

Although alpha-lipoic acid is stable to gamma-sterilization and temperatures up to 60° C., it may undergo partial decomposition in some storage conditions, like high humidity and low temperature, which is accompanied by an unpleasant odor due to its sulfur content. However, conversion of alpha-lipoic acid into a salt derivative, such as sodium lipoate, or the use of polymer barriers in the wound dressing 110 mitigates the odor issues. For example, a lipoic acid derivative may be converted to a salt at a pH of about 6 to about 8. Within this pH range lipoic acid derivatives, such as alpha-lipoic acid, can be efficiently converted to a salt to reduce odor without significant loss of antioxidant activity. Thus, in certain aspects, the invention provides compositions having reduced odor properties comprising a pharmaceutically acceptable salt of a lipoic acid derivative (e.g., sodium lipoate).

When the alpha-lipoic acid is converted enzymatically into dihydrolipoic acid, the dihydrolipoic acid is more potent than alpha-lipoic acid at neutralizing superoxide radicals, hydroperoxy radicals, hydroxyl radicals, and other major ROS and the antioxidant activity of the lipoic acid actually increases in the cells. Application of stable molecule of alpha-lipoic acid, which converts in the body into extremely potent antioxidant is highly advantageous from the handling and shelf-life perspectives. Thus, in certain aspects, a lipoic acid derivative for use according to the invention may be a lipoic acid prodrug that is converted into an active antioxidant in vivo.

Excessive MMP activity at a tissue site can also be addressed by providing a biologically active composition comprising a sacrificial proteolytic enzyme substrate, such as protein, protein hydrolysate, or combinations thereof. For example, a sacrificial proteolytic enzyme substrate can comprise keratin, collagen, elastin, gelatin, casein, albumin, fibrinogen, fibronectin, soy protein, wheat protein, corn protein, milk proteins and/or hydrolysates thereof (see, e.g., U.S. Pat. No. 6,500,443, incorporated herein by reference). In certain embodiments, proteins for use as sacrificial substrates are hydrolyzed or partially hydrolyzed by treatment with a strong acid or base. Such treatment can fragment the subject proteins and generate more accessible peptide sequence to bind to proteolytic enzymes.

The most prevalent MMPs in chronic wounds are the gellatinase proteases, MMP-2 and MMP-9 that more readily target the hydrolyzed or denatured form of collagen known as "gelatin." Thus, in certain aspects, a biologically active composition for use as described here further comprises a collagen, such as a hydrolyzed collagen (e.g., gelatin). Gelatin can be processed from a variety of sources including, but not limited to, bovine skin, pig skin and bone material. Depending on the hydrolysis methods employed in manufacture, the gelatin may be defined as a type A or type B gelatin. One advantage of using a gelatin rather than, or in addition to, collagen is that gelatin includes exposed peptide sequences that serve as signals for protease binding. Accessibility of signaling sequences in the native collagen molecule is diminished due to triple-helix structure of native collagen molecule, where polypeptide chains are bound with strong hydrogen bonds. Thus, in certain aspects, a biologically active composition is defined as not comprising collagen. In the case of gelatin, on the other hand, signaling sequences are readily exposed to proteases making it more efficient as a sacrificial substrate.

A primary constraint against using gelatin in wound dressings is insufficient mechanical integrity and inability to maintain dressing shape in wound environment as is possible with natural collagen. However, if gelatin is applied as a coating onto another porous material, such as polyurethane foam, which will provide structural support, such dressing with gelatin can be an excellent choice as an MMP sacrificial substrate. Gelatin for use in biologically active compositions will, nonetheless, need to comprise sufficient gel strength to form an adherent layer on a porous material without causing the material to become overly stiff. Accordingly, gelatin for use in biologically active compositions can comprise a bloom value of between about 150-300 g, between about 200-250 g or about 225 g.

Additionally, gelatin is an excellent oxygen barrier, which is important for stability of molecules that could be incorporated in the dressings, such as antioxidants and oxygen sensitive proteins and peptides. Thus, the scaffold 140 may be a polyurethane foam as described above that is coated with gelatin to provide the reduced pressure dressing 110 with a sacrificial substrate for MMPs. Biologically active compositions may, for example, comprise 0.1% to 25%, 1% to 10% or about 6%, 8%, 10%, 15% or 20% w/w gelatin.

In certain aspects, a biologically active composition, such as a composition coated on a porous material is sterilized by irradiation. A skilled worker will recognize that such irradiation can alter the amount of cross-linking within proteins in the composition. Thus, in cases where composition comprises a sacrificial proteolytic enzyme substrate that is a protein, such as gelatin, the amount of irradiation may be adjusted not only to achieve sterilization but also to achieve a desired level of protein cross-linking. For example, a gelatin with a relatively low bloom value can be used in a coating and then subjected to irradiation to increase the effective bloom value of the gelatin coating by further cross-linking the protein. In certain aspects, biologically active compositions and/or wound dressings according to the invention are subjected to gamma irradiation, such as between about 10-80 Gy, about 20-60 Gy or about 30-50 Gy of radiation.

Biologically active compositions may be formulated as a solution, a spray, a cream, a gel or coating provided on a scaffold. Such compositions may be formulated for time-controlled release of the lipoic acid derivative. For example, the formulation may be formulated such that the lipoic acid derivative is released over a period of about 12 hours, 24 hours, 2 days, 3 days 4 days or 1 or more weeks.

In certain aspects, a biologically active composition is coated onto the surface and into the pores of a scaffold 140, as detailed above. Methods for coating such a scaffold may, for example, comprise the steps of (i) saturating a porous substrate material with a solution comprising the components of a biologically active composition; and (ii) drying the porous substrate thereby producing a wound healing scaffold coated with a biologically active composition. For example, the coating solution may comprise a lipoic acid derivative (e.g., alpha-lipoic acid or sodium lipoate) and gelatin. In certain aspects, the substrate material is dried such that the resulting wound healing scaffold comprises a moisture content of less than about 5%.

Biologically active compositions disclosed herein may further comprise other biologically active molecules such as antimicrobial agents, growth factors, proteinase inhibitors, chelating agent or preservatives. For example, in certain aspects the composition additionally comprises a metal chelating agent capable of reducing MMP activity, such as EDTA. Antimicrobial agents may also be used in compositions according to the invention. For example, the composition may include antibiotics, antifungal agents or more general antimicrobials. Antimicrobial compounds compatible with lipoic acid formulation include, but are not limited to, non-ionic silver, polyhexamethylene biguanide, chlorhexidine, benzalconium chloride, triclosan and others.

As described below, the combination of a lipoic acid derivative and gelatin promotes healing or prophylaxis of chronic ulcers by regulating level of ROS and matrix metalloproteinases (MMP's) at the ulcer site. The balance between reactive oxygen species, proteolytic enzymes and their inhibitors is critical to the persistence and healing of chronic ulcers, and that the alpha-lipoic acid corrects this balance in chronic ulcers. Alpha-lipoic acid, for example, inhibits the influx of inflammatory cells to a wound site by inhibiting the transcription of genes for adhesion molecules such as ICAM-1 and other adhesion molecules on inflammatory cells and endothelial cells. The alpha-lipoic acid inhibits the activation of nuclear transcription factors such as NF-κB, which controls the transcription of the MMP-9 gene, adhesion molecule genes such as ICAM-1, and inflammatory mediator genes such as TNF-alpha. Finally, alpha-lipoic acid can interfere with the inflammatory mediators such as leukotrienes.

Biologically active compositions may be infused within, or coated on, the scaffold 140. For example, the composition of alpha-lipoic acid may be coated on a woven, non-woven, or knitted fabric material. Alternatively, the alpha-lipoic acid may be dispersed within a bioresorbable polymeric film, sponge, or foam for sustained release at the wound 102. The alpha-lipoic acid may also be coated with gelatin on a polyurethane reticulated foam as described in the following Example.

The formulation of lipoic acid and gelatin applied as a coating on the open-cell reticulated polyurethane foam pads provides unique combination of effects and is highly effective for healing of chronic wounds. The formulation can be used in combination with negative pressure wound therapy, which is known to be highly effective in stimulating growth of granulation tissue, reducing infection and maintaining proper moisture balance in the wound. Addition gelatin and lipoic acid and EDTA to the dressing specifically addresses healing of chronic wounds removing barriers to normal healing such as abnormally high levels of ROS and MMPs. It should be noted that MMP aspect of wound healing is addressed by formulations described in herein from several perspectives, i.e., the reduction of ROS levels to affect recruitment of MMPs, the addition of EDTA to prevent MMP from activation, and gelatin to service as sacrificial substrate for MMPs preserving newly formed granulation tissue.

EXAMPLES

The following examples are included to demonstrate certain embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Polyurethane open-cell reticulated foam pads were selected as the scaffold 140 and were immersed in a solution containing 1.5 wt % of alpha-lipoic acid and 4.5 wt % 225-bloom beef gelatin (and, where applicable, 0.3% EDTA). Gelatin was used as a biocompatible binding agent with good oxygen barrier and sustained release properties for alpha-lipoic acid as well as for its ability to act as a sacrificial substrate for surrounding gelatinases. Alpha-lipoic acid was pre-dissolved in ethanol and then mixed into the final solution. The foam pads were immersed for a sufficient amount of time to coat the pathways formed within the open-cell reticulated foam as described above with respect to the scaffold 140. After immersion, the foam pads were withdrawn, compressed to remove excess solution, and dried to a constant weight. In some cases, sodium benzoate was added to the formulation as a preservative. Dried foams comprised, by weight, 2% alpha-lipoic acid, 6% gelatin and, where applicable, 0.4% EDTA.

Figure 7:
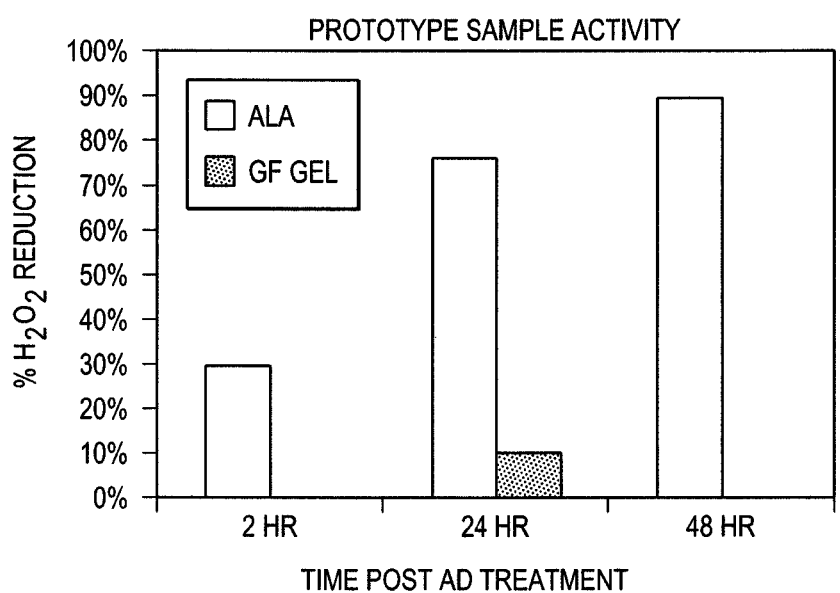
FIG. 7 is a graph showing antioxidant activity for scaffolds containing alpha-lipoic acid.
Figure 8:
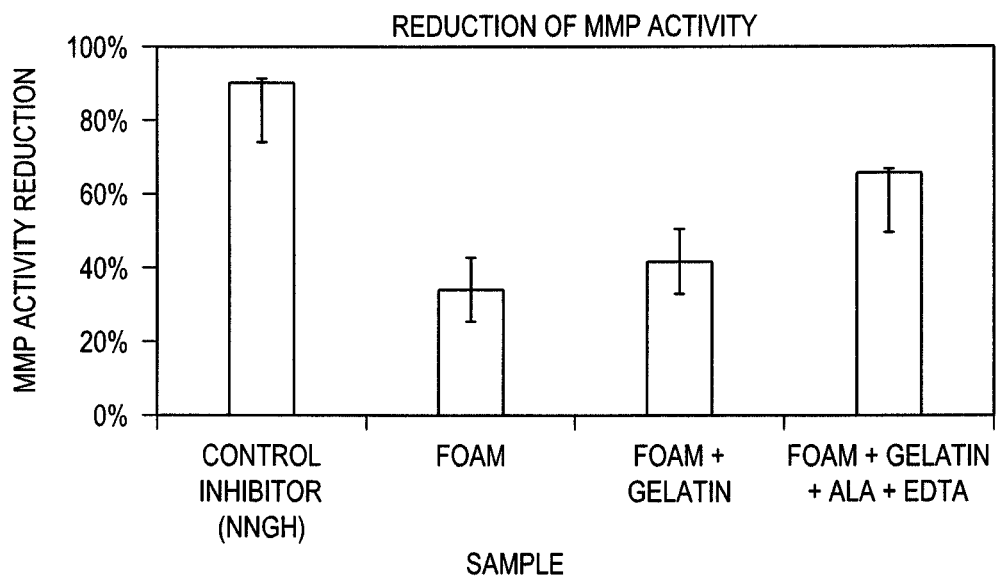
FIG. 8 is a chart showing the reduction of MMP activity for scaffolds containing alpha-lipoic acid and gelatin as compared to controls.
Figure 9:
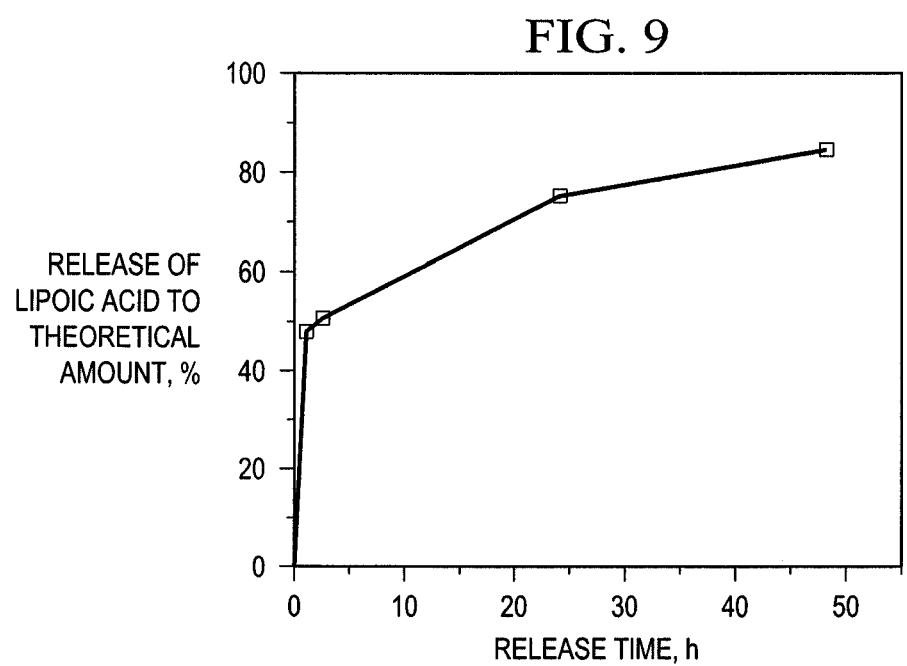
FIG. 9 is a chart showing the release profile of alpha-lipoic acid from coating on a scaffold.

A National Diagnostics Hydrogen Peroxide Assay Kit was used to evaluate the antioxidant properties of foam pads and the formulated coated foam pads containing alpha-lipoic acid. Foam pads coated only with gelatin were used as controls. FIG. 7 is a graph showing the percentage of hydrogen peroxide reduction due to reaction with alpha-lipoic acid. An MMP-9 Colorimetric Drug Discovery Kit (Biomol) was used to evaluate the MMP inhibiting/inactivating ability of the formulated foam pads containing alpha-lipoic acid/gelatin (ALA) and gelatin alone (GF GEL). The controls were uncoated foam pads and known potent MMP inactivating drug, NNGH ($C_{13}H_{20}N_2O_5S$, available from Enzo® Life Sciences). FIG. 8 is a graph showing that gelatin-coated foam pads inhibit MMP activity, but the combination of gelatin and ALA along with the EDTA (described in Example 2) are much more potent than gelatin alone. FIG. 9 is a graph showing the release of alpha-lipoic acid from the coating on the foam pads. The coating delivers approximately 70% of the total alpha-lipoic acid within the first day, while the remaining alpha-lipoic acid is released during the next 2-3 days.

Example 2

Chelating agents like ethlenediaminetetraacetic acid (EDTA) were added to the dipping solution described in Example 1. The addition of EDTA to wound dressings prevents MMP from activation chelating zinc ions essential for activation of pro-MMPs.

Example 3

A solution of sodium hydroxide can be added to the dipping solution described in Examples 1-2 to convert lipoic acid into sodium lipoate. The pH of resulting solution should be in the range between 6 and 8. The conversion of lipoic acid into sodium lipoate eliminates the risk of development of sulphur odor in the coated foams.

Example 4

Coated polyurethane foam (GranuFoam®) scaffolds described above in Examples 1-2 were further assayed for their ability to reduce MMP activity as compared to noncoated collagen based scaffold such as the Biostep™ and Promogran™ products. The results from two separate experiments are presented below in Tables 1 and 2 and demonstrate that the coated scaffolds reduced MMP activity similarly to collagen scaffolds, even though the coated scaffolds only comprised 10% by weight biologically active layer.

TABLE 1

| Dressing treatment | % MMP-9 activity reduction* | Standard deviation |
| --- | --- | --- |
| NNGH | 90.2 | 1.2 |
| Foam | 34.5 | 9.6 |
| Foam + gelatin | 42.2 | 8.4 |
| Foam + gelatin + ALA + EDTA | 65.8 | 0.0 |
| Promogran ™ | 68.7 | 0.5 |
| Biostep ™ | 82.2 | 1.8 |

*All values indicate the amount of MMP-9 activity reduction as compared to control samples with no MMP-9 inhibitor activity.
ALA indicates alpha-lipoic acid coating.

TABLE 2

| Dressing treatment | % MMP-9 activity reduction* | Standard deviation |
| --- | --- | --- |
| NNGH | 103.8% | 2.1 |
| Foam | 27.1% | 0.2 |
| Foam + gelatin | 72.6% | 21.8 |
| Foam + gelatin + EDTA | 54.5% | 3.5 |
| Foam + gelatin + ALA + EDTA | 90.4% | 1.9 |
| Promogran ™ | 100.8% | 4.5 |
| Biostep ™ | 104.6% | 3.0 |

*All values indicate the amount of MMP-9 activity reduction as compared to control samples with no MMP-9 inhibitor activity.
ALA indicates alpha-lipoic acid coating.

Example 5

The radiation stability of alpha-lipoic acid coated scaffolds described above were assessed by measuring the effectiveness of scaffold at decreasing ROS after gamma irradiation. Briefly, irradiated and control scaffolds were treated with 20 µM $H_2O_2$. Peroxide concentration was then measured using a TBR4100 with HPO-100 sensor (available from World Precision Instruments) at 2 hours or 24 hours after treatment. The results of these studies are summarized in Table 3. Results represent the average peroxide reduction measured in 10 replicates. As shown, the alpha-lipoic acid coating remained highly active (i.e., as an antioxidant) even after extensive irradiation.

TABLE 3

| Dressing irradiation treatment | ROS reduction 2 hr. | ROS reduction 24 Hours |
| --- | --- | --- |
| Foam alone control (0 Gy) | 19% | 31% |
| 30 Gy | 45% | 83% |
| 40 Gy | 55% | 87% |
| 50 Gy | 59% | 86% |
| 60 Gy | 59% | 85% |

While the systems and methods of the present invention have been described with reference to tissue growth and healing in human patients, it should be recognized that these systems and methods for applying reduced pressure tissue treatment can be used in any living organism in which it is desired to promote tissue growth or healing. Similarly, the systems and methods of the present invention may be applied to any tissue, including without limitation bone tissue, adipose tissue, muscle tissue, dermal tissue, vascular tissue, connective tissue, cartilage, tendons, or ligaments. While the healing of tissue may be one focus of applying reduced pressure tissue treatment as described herein, the application of reduced pressure tissue treatment may also be used to generate tissue growth in tissues that are not diseased, defective, or damaged. For example, it may be desired to apply reduced pressure tissue treatment to grow additional tissue at a tissue site that can then be harvested. The harvested tissue may be transplanted to another tissue site to replace diseased or damaged tissue, or alternatively the harvested tissue may be transplanted to another patient.

Although the present invention and its advantages have been disclosed in the context of certain illustrative, non-limiting embodiments, it should be understood that various changes, substitutions, permutations, and alterations can be made without departing from the scope of the invention as defined by the appended claims.

We claim:

1. A dressing for treating a tissue site, comprising:
   a manifold comprising an open-cell foam having a plurality of flow channels adapted to distribute reduced pressure through the manifold; and
   a composition for reducing excessive matrix metalloprotease activity coated on at least a portion of the manifold, wherein the composition comprises:
     a gelatin substrate as a sacrificial proteolytic enzyme substrate,
     a lipoic acid derivative, and
     a chelating agent capable of reducing matrix metalloprotease activity.

2. The dressing of claim 1, wherein the gelatin substrate comprises exposed peptide sequences adapted to serve as signals for matrix metalloprotease binding.

3. The dressing of claim 1, wherein the lipoic acid derivative comprises a pharmaceutically-acceptable salt.

4. The dressing of claim 1, wherein the lipoic acid derivative is alpha-lipoic acid or a pharmaceutically-acceptable salt of alpha-lipoic acid.

5. The dressing of claim 1, wherein the composition comprises 0.1% to 25% w/w gelatin substrate.

6. The dressing of claim 1, wherein the composition comprises 0.1% to 5% w/v lipoic acid derivative.

7. The dressing of claim 1, wherein the composition further comprises an antimicrobial agent, a growth factor, or a preservative.

8. The dressing of claim 7, wherein the antimicrobial agent is non-ionic silver, polyhexamethylene biguanide, chlorhexidine, benzalkonium chloride, or triclosan.

9. The dressing of claim 1, wherein the chelating agent comprises ethylenediaminetetraacetic acid.

10. The dressing of claim 1, wherein the manifold comprises an open-cell polyurethane foam.

11. The dressing of claim 1, further comprising a scaffold adapted to be positioned between the manifold and the tissue site, wherein the scaffold has a plurality of passages.

12. The dressing of claim 11, further comprising a release layer adapted to be positioned between the scaffold and the manifold.

13. A composition for applying to a tissue dressing for reducing excessive matrix metalloprotease activity, comprising:
   a sacrificial matrix metalloprotease substrate comprising gelatin and having exposed peptide sequences adapted to serve as signals for matrix metalloprotease binding;

a lipoic acid derivative; and a chelating agent comprising ethylenediaminetetraacetic acid for reducing matrix metalloprotease activity.

14. The composition of claim 13, wherein the lipoic acid derivative comprises a pharmaceutically-acceptable salt.

15. The composition of claim 13, wherein the lipoic acid derivative is alpha-lipoic acid or a pharmaceutically-acceptable salt of alpha-lipoic acid.

16. The composition of claim 13, wherein the composition comprises 0.1% to 25% w/w gelatin substrate.

17. The composition of claim 13, wherein the composition comprises 0.1% to 5% w/v lipoic acid derivative.

18. The composition of claim 13, further comprising an antimicrobial agent, a growth factor, or a preservative.

19. A wound dressing, comprising:

a porous polyurethane material; and a composition comprising a sacrificial proteolytic enzyme substrate and a lipoic acid derivative, the composition provided on at least a portion of the porous polyurethane material;

wherein the lipoic acid derivative is a dihydrolipoic acid comprising the structure:

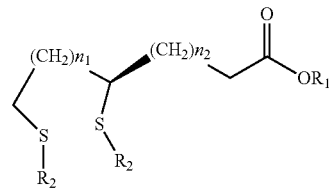

wherein n1 and n2 are, independently, $C_1$-$C_{10}$ alkyl;

$R_1$ is H, $C_1$-$C_{10}$ alkyl, $C_6$-$C_{14}$ aryl, an alkyl ammonium or a protonated amino acid; and $R_2$ is H, $C_1$-$C_{10}$ alkyl or $C_6$-$C_{14}$ aryl.

20. The wound dressing of claim 19, wherein the composition further comprises an antimicrobial agent, a growth factor, a proteinase inhibitor, a chelating agent or a preservative.

* * * * *